(12) United States Patent
Lorenzo

(10) Patent No.: US 11,154,302 B2
(45) Date of Patent: Oct. 26, 2021

(54) ANEURYSM OCCLUSION DEVICE

(71) Applicant: DEPUY SYNTHES PRODUCTS, INC., Raynham, MA (US)

(72) Inventor: Juan Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 398 days.

(21) Appl. No.: 14/230,426

(22) Filed: Mar. 31, 2014

(65) Prior Publication Data

US 2015/0272589 A1 Oct. 1, 2015

(51) Int. Cl.
*A61B 17/12* (2006.01)
*A61B 17/00* (2006.01)

(52) U.S. Cl.
CPC .... *A61B 17/12113* (2013.01); *A61B 17/1204* (2013.01); *A61B 17/1214* (2013.01); *A61B 17/12145* (2013.01); *A61B 17/12172* (2013.01); *A61B 2017/00526* (2013.01); *A61B 2017/12054* (2013.01)

(58) Field of Classification Search
CPC ....... A61B 17/12022; A61B 17/12168–12177; A61B 17/12113; A61B 17/1204; A61B 17/12145; A61B 2017/1205; A61B 2017/12054; A61F 2/01; A61F 2002/011
USPC ........................................................ 606/200
See application file for complete search history.

(56) References Cited

U.S. PATENT DOCUMENTS

| | | |
|---|---|---|
| 2,849,002 A | 8/1958 | Oddo |
| 3,480,017 A | 11/1969 | Shute |
| 4,085,757 A | 4/1978 | Pevsner |
| 4,282,875 A | 4/1981 | Serbinenko et al. |
| 4,364,392 A | 12/1982 | Strother et al. |
| 4,395,806 A | 8/1983 | Wonder et al. |

(Continued)

FOREIGN PATENT DOCUMENTS

| | | |
|---|---|---|
| CA | 2395796 A1 | 7/2001 |
| CA | 2 431 594 A1 | 9/2002 |

(Continued)

OTHER PUBLICATIONS

Altes et al., Creation of Saccular Aneurysms in the Rabbit: A Model Suitable for Testing Endovascular Devices. AJR 2000; 174: 349-354.

(Continued)

*Primary Examiner* — Katrina M Stransky
*Assistant Examiner* — Mikail A Mannan
(74) *Attorney, Agent, or Firm* — Troutman Pepper Hamilton Sanders LLP

(57) ABSTRACT

An occlusion device suitable for endovascular treatment of an aneurysm in a blood vessel in a patient, including a substantially tubular structure having a proximal end region and a distal end region, having a first, expanded condition and a second, collapsed condition. The device has dimensions in the second, collapsed condition suitable for insertion through vasculature of the patient and through a neck of the aneurysm. The device further includes a control ring having a substantially annular body disposed on the proximal end region of the structure and at least substantially circumscribing the proximal end region to prevent radial expansion of the proximal end region and to provide an engagement feature during manipulation of the occlusion device.

18 Claims, 6 Drawing Sheets

(56) References Cited

U.S. PATENT DOCUMENTS

| | | |
|---|---|---|
| 4,517,979 A | 5/1985 | Pecenka |
| 4,545,367 A | 10/1985 | Tucci |
| 4,836,204 A | 6/1989 | Landymore et al. |
| 4,991,602 A | 2/1991 | Amplatz et al. |
| 5,002,556 A * | 3/1991 | Ishida ............ A61B 17/12109 604/103.1 |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,891,128 A | 4/1999 | Gia et al. |
| 5,916,235 A | 6/1999 | Guglielmi |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,410,482 B2 | 8/2008 | Murphy |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,992,568 B2 | 3/2015 | Duggal et al. |
| 8,998,947 B2 | 3/2015 | Aboytes et al. |
| 8,974,512 B2 | 4/2015 | Aboytes et al. |
| 9,055,948 B2 | 6/2015 | Jaeger et al. |
| 9,107,670 B2 | 8/2015 | Hannes et al. |
| 9,161,758 B2 | 10/2015 | Figulla et al. |
| 9,232,992 B2 | 1/2016 | Heidner et al. |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |

(56) References Cited

U.S. PATENT DOCUMENTS

| | | | |
|---|---|---|---|
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1* | 9/2003 | Murphy ........... A61B 17/12022 606/1 |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1* | 7/2005 | Petersen ........... A61F 2/01 606/200 |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Guterman |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1* | 11/2006 | McCartney ........... A61B 8/0841 604/19 |
| 2007/0088387 A1 | 4/2007 | Eskridge et al. |
| 2007/0106311 A1 | 5/2007 | Wallace |
| 2007/0208376 A1 | 6/2007 | Meng |
| 2007/0162071 A1* | 7/2007 | Burkett ........... A61F 2/01 606/200 |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1* | 11/2007 | Amplatz ........... A61B 17/0057 606/200 |
| 2007/0288083 A1 | 12/2007 | Hines |
| 2008/0097495 A1 | 4/2008 | Feller, III et al. |
| 2008/0103505 A1 | 5/2008 | Fransen |
| 2008/0281350 A1* | 11/2008 | Sepetka ........... A61B 17/0057 606/200 |
| 2009/0036877 A1* | 2/2009 | Nardone ........... A61B 17/12022 606/1 |
| 2009/0062841 A1 | 3/2009 | Amplatz et al. |
| 2009/0099647 A1* | 4/2009 | Glimsdale ........... A61B 17/0057 623/1.35 |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijikema |
| 2010/0063582 A1 | 3/2010 | Rudakov |
| 2010/0069948 A1 | 3/2010 | Veznedaroglu |
| 2010/0168781 A1 | 7/2010 | Berenstein |
| 2010/0324649 A1 | 12/2010 | Mattsson et al. |
| 2011/0046658 A1 | 2/2011 | Conner et al. |
| 2011/0054519 A1* | 3/2011 | Neuss ........... A61B 17/0057 606/213 |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1* | 2/2013 | Chu ........... A61L 31/14 604/509 |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden |
| 2013/0261658 A1 | 10/2013 | Lorenzo et al. |
| 2013/0261730 A1* | 10/2013 | Bose ........... A61B 17/12118 623/1.12 |
| 2013/0274863 A1 | 10/2013 | Cox et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |

(56) References Cited

U.S. PATENT DOCUMENTS

| | | |
|---|---|---|
| 2014/0200607 A1 | 7/2014 | Sepetka et al. |
| 2014/0257360 A1 | 9/2014 | Keillor |
| 2014/0277013 A1 | 9/2014 | Sepetka et al. |
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0114350 A1 | 4/2017 | dos Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1 | 5/2018 | Connor |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0365385 A1 | 12/2019 | Gorochow et al. |
| 2020/0268365 A1 | 8/2020 | Hebert et al. |

FOREIGN PATENT DOCUMENTS

| | | |
|---|---|---|
| CA | 2598048 A1 | 5/2008 |
| CN | 204 683 687 U | 7/2015 |
| DE | 102008015781 A1 | 10/2009 |
| DE | 102010053111 A1 | 6/2012 |
| DE | 102011102955 | 12/2012 |
| DE | 102009058132 B4 | 7/2014 |
| DE | 202008018523 U1 | 4/2015 |
| DE | 102013106031 | 7/2015 |
| EP | 09027048 | 3/1999 |
| EP | 1054635 B1 | 11/2000 |
| EP | 1295563 B1 | 3/2003 |
| EP | 1441649 B1 | 8/2004 |
| EP | 1483009 B1 | 8/2004 |
| EP | 1494619 B1 | 1/2005 |
| EP | 1527753 B1 | 5/2005 |
| EP | 1569565 B1 | 7/2005 |
| EP | 1574169 B1 | 9/2005 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 3/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |

(56) References Cited

FOREIGN PATENT DOCUMENTS

| | | | |
|---|---|---|---|
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 | 9/2013 |
| JP | 2016-502925 A | 2/2015 |
| WO | WO9641589 A1 | 12/1996 |
| WO | 99/05977 A1 | 2/1999 |
| WO | WO9908607 A2 | 2/1999 |
| WO | WO 9930640 A1 | 6/1999 |
| WO | 2003073961 A1 | 9/2003 |
| WO | WO 2003073961 A1 | 9/2003 |
| WO | WO 03/086240 A1 | 10/2003 |
| WO | WO2005020822 A1 | 3/2005 |
| WO | WO 2005074814 A2 | 8/2005 |
| WO | WO 2005117718 A1 | 12/2005 |
| WO | WO2006034149 A2 | 3/2006 |
| WO | WO2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO2009048700 A1 | 4/2009 |
| WO | WO2009105365 A1 | 8/2009 |
| WO | WO2009132045 A2 | 10/2009 |
| WO | WO2009135166 A2 | 11/2009 |
| WO | WO2010030991 A1 | 3/2010 |
| WO | WO2011057002 A2 | 5/2011 |
| WO | WO2012032030 A1 | 3/2012 |
| WO | WO2012099704 A2 | 7/2012 |
| WO | WO2012099909 A2 | 7/2012 |
| WO | WO2012113554 A1 | 8/2012 |
| WO | WO2013016618 A2 | 1/2013 |
| WO | WO2013025711 A1 | 2/2013 |
| WO | WO2013109309 A1 | 7/2013 |
| WO | WO 2013159065 A1 | 10/2013 |
| WO | WO2014029835 A1 | 2/2014 |
| WO | WO2014110589 A1 | 7/2014 |
| WO | WO2014137467 A1 | 9/2014 |
| WO | WO2015073704 A1 | 5/2015 |
| WO | WO2015160721 A1 | 10/2015 |
| WO | WO2015166013 A1 | 11/2015 |
| WO | WO 2015171268 A2 | 11/2015 |
| WO | WO2015184075 A1 | 12/2015 |
| WO | WO2015187196 A1 | 12/2015 |
| WO | 2016/044647 A2 | 3/2016 |
| WO | WO2016107357 A1 | 7/2016 |
| WO | WO16137997 A1 | 9/2016 |
| WO | WO 2017/161283 A1 | 9/2017 |
| WO | WO 2018051187 A1 | 3/2018 |
| WO | WO 2012/034135 A1 | 3/2021 |

OTHER PUBLICATIONS

Schaffer, Advanced Materials & Processes, Oct. 2002, pp. 51-54.
Extended European Search Report issued in corresponding European Patent Application No. 19196722.3 dated Jan. 22, 2020.
Extended European Search Report issued in corresponding European Patent Application No. 19 21 5277 dated May 12, 2020.

\* cited by examiner

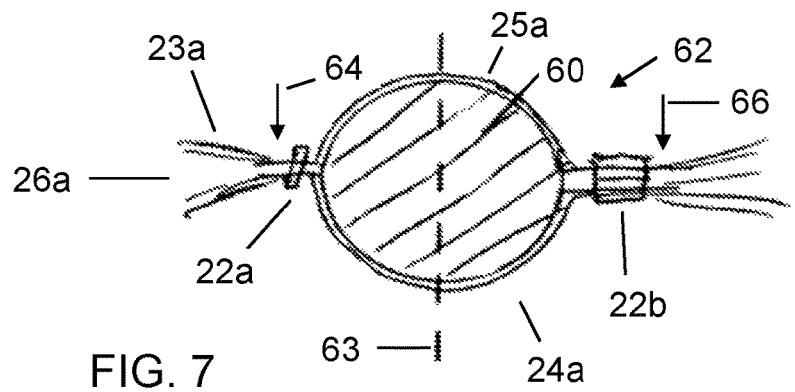
FIG. 7
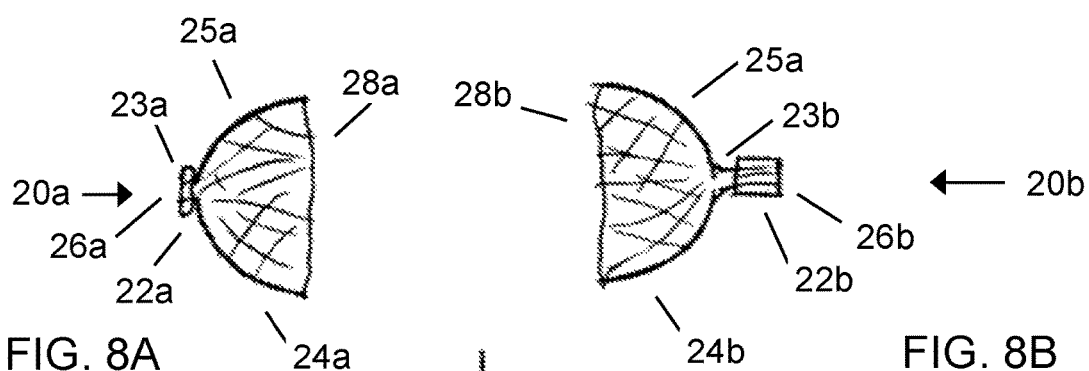
FIG. 8A
FIG. 8B
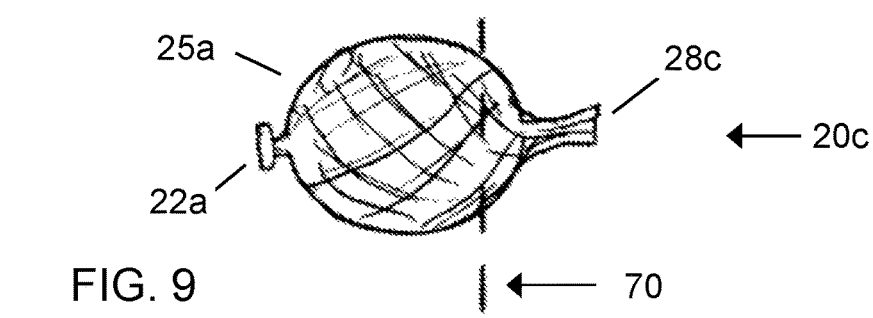
FIG. 9
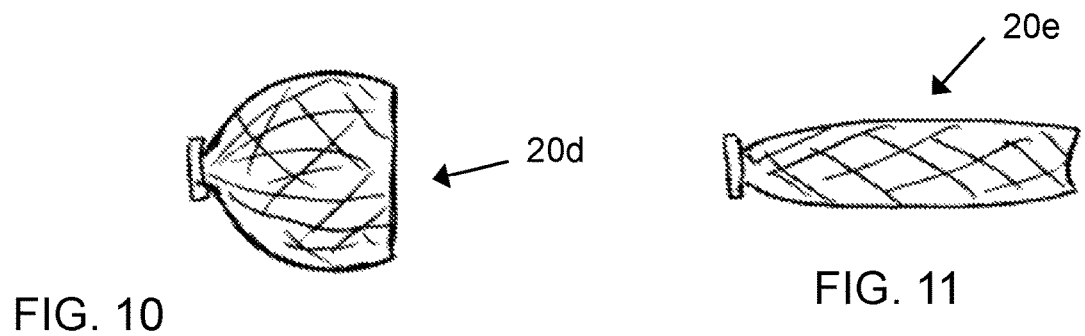
FIG. 10
FIG. 11

ANEURYSM OCCLUSION DEVICE

BACKGROUND OF THE INVENTION

1. Field of the Invention

The invention relates to implants within body vessels and more particularly to occlusion devices for small vascular openings such as a neck of an aneurysm.

2. Description of the Related Art

Vascular disorders and defects such as aneurysms and other arterio-venous malformations are especially difficult to treat when located near critical tissues or where ready access to a malformation is not available. Both difficulty factors apply especially to cranial aneurysms. Due to the sensitive brain tissue surrounding cranial blood vessels and the restricted access, it is very challenging and often risky to surgically treat defects of the cranial vasculature.

In the treatment of aneurysms by endovascular implants, the goal is to exclude the internal volume of the aneurysm sac from arterial blood pressure and flow. As long as the interior walls of the aneurysm are subjected to blood pressure and/or flow, there is a risk of the aneurysm rupturing.

Non-surgical treatments include vascular occlusion devices such as embolic coils deployed using catheter delivery systems. In a currently preferred procedure to treat a cranial aneurysm, the distal end of an embolic coil delivery catheter is initially inserted into non-cranial vasculature of a patient, typically through a femoral artery in the groin, and guided to a predetermined delivery site in a blood vessel within the cranium. The aneurysm sac is then filled with embolic material that causes formation of a solid, thrombotic mass that protects the walls from blood pressure and flow. Preferably, the thrombotic mass substantially restores the original blood vessel shape along the plane of the aneurysm's neck. The neck plane is an imaginary surface where the intima of the blood vessel would be if not for formation of the aneurysm. However, simply utilizing embolic coils is not always effective at treating aneurysms as re-canalization of the aneurysm and/or coil compaction can occur over time.

A bag for use in an aneurysm sac is described by Greenhalgh in U.S. Pat. Nos. 6,346,117 and 6,391,037, and an aneurysm neck obstruction device is shown in U.S. Pat. No. 6,454,780 by Wallace. Detachable neck bridges are disclosed by Abrams et al. in U.S. Pat. No. 6,036,720 and by Murphy et al. in U.S. Pat. No. 7,410,482 for example. Preferably, one or more embolic coils are delivered within or through the neck bridges or other obstruction devices to fill the sac of the aneurysm.

Yet another type of vaso-occlusive device is illustrated in U.S. Pat. No. 5,645,558 by Horton as having one or more strands of flexible material which are wound to form a generally spherical or ovoid vaso-occlusive structure when relaxed after being placed in a vascular cavity such as an aneurysm or fistula. Similarly, U.S. Pat. No. 5,916,235 by Guglielmi cites earlier patents describing detachable coils and then discloses an expandable cage as a vaso-occlusive structure that can receive and retain one or more coils after the cage is expanded within an aneurysm. A self-expandable aneurysm filling device is disclosed in US Patent Publication No. 2010/0069948 by Veznedaroglu et al.

It is therefore desirable to have a retrievable, repositionable device that cooperates with one or more embolic coils or other vaso-occlusive structure to effectively occlude a neck of an aneurysm or other arterio-venous malformation in a blood vessel.

SUMMARY OF THE INVENTION

An object of the present invention is to provide an improved occlusion device which substantially blocks flow into an aneurysm in a blood vessel.

Another object of the present invention is to provide such an occlusion device which can be repositioned or retrieved from a sac of an aneurysm.

This invention features an occlusion device suitable for endovascular treatment of an aneurysm in a blood vessel in a patient, including a substantially tubular structure having a proximal end region and a distal end region, having a first, expanded condition and a second, collapsed condition. The device has dimensions in the second, collapsed condition suitable for insertion through vasculature of the patient and through a neck of the aneurysm. The device further includes a control ring having a substantially annular body disposed on the proximal end region of the structure and at least substantially circumscribing the proximal end region to prevent radial expansion of the proximal end region and to provide an engagement feature during manipulation of the occlusion device.

In a number of embodiments, the control ring defines an inner passage, such as a channel established by an inner sleeve, through which at least one embolic coil is insertable into the aneurysm. Preferably, at least a portion of the proximal end region of the tubular structure defines a plurality of openings having a sufficiently small size to enhance occlusion of the aneurysm. In some embodiments, the tubular structure cooperates with at least one vaso-occlusion structure such as a collapsible cage-like device.

In certain embodiments, the occlusive device is capable of being utilized in combination with a delivery member defining an inner lumen and having a distal end region carrying a grabber having at least two finger elements, each finger element defining a gripping region to mechanically engage the control ring. In one embodiment, the grabber is formed of a metallic material and the gripping regions are notches formed in the finger elements, each notch being sized to mechanically engage a portion of the control ring. The combination may further include a catheter having an inner lumen through which the delivery tube is insertable and translatable relative to the catheter.

This invention may also be expressed as a method of treating an aneurysm in a blood vessel in a patient, the method including selecting an occlusion device with a structure having a substantially tubular structure having a proximal end region and a distal end region, having a first, expanded condition and a second, collapsed condition, and having dimensions in the second, collapsed condition suitable for insertion through vasculature of the patient and through a neck of the aneurysm. The device further includes a control ring having a substantially annular body disposed on the proximal end region of the structure and at least substantially circumscribing the proximal end region to prevent radial expansion of the proximal end region.

In some embodiments, the method further includes mechanically engaging the control ring with a grabber on a delivery tube to enable manipulation of the occlusion device, drawing the occlusion device into a catheter carrying the delivery tube to force the occlusion device into the collapsed condition, inserting the catheter with the occlusion device into vasculature of the patient to reach the region of the aneurysm in the blood vessel, and positioning the occlusion device within the aneurysm.

In certain embodiments, the method additionally includes delivering at least one embolic coil through the delivery tube and through the control ring to secure the occlusion device within the aneurysm to occlude flow into the aneurysm, and mechanically releasing the control ring and withdrawing the catheter and the delivery tube from the patient. In yet other embodiments, the method further includes selecting the occlusive device to be attached to a collapsible cage-like vaso-occlusive structure, and positioning the occlusive device within the aneurysm includes utilizing the vaso-occlusive structure to secure the proximal end region of the tubular structure across the neck of the aneurysm

BRIEF DESCRIPTION OF THE DRAWINGS

In what follows, preferred embodiments of the invention are explained in more detail with reference to the drawings and photographs, in which:

FIG. 7 is a schematic cross-sectional view of a spherical mandrel establishing the first, expanded condition for at least one an occlusion device according to the present invention;

FIGS. 8A and 8B are schematic side views of two hemi-spherical occlusion devices according to the present invention derived from the occlusion device of FIG. 7;

FIG. 9 is a schematic side view of a single occlusion device after the mandrel of FIG. 7 has been removed;

FIG. 10 is a schematic side view similar to FIG. 9 after a distal portion of the occlusion device has been removed to generate an alternative open configuration;

FIG. 11 is a side view similar to FIG. 10 of an alternative occlusion device formed utilizing an elliptical, lozenge-shaped mandrel;

DETAILED DESCRIPTION OF THE PRESENTLY PREFERRED EMBODIMENTS

This invention may be accomplished by an occlusion device suitable for endovascular treatment of an aneurysm in a blood vessel in a patient, with a substantially tubular structure having a proximal end region and a distal end region, having a first, expanded condition and a second, collapsed condition. The device has dimensions in the second, collapsed condition suitable for insertion through vasculature of the patient, utilizing a catheter such as a microcatheter, and through a neck of the aneurysm. The device further includes a control ring having a substantially annular body disposed on the proximal end region of the structure and at least substantially circumscribing the proximal end region to prevent radial expansion of the proximal end region and to provide an engagement feature during manipulation of the occlusion device.

The control ring is releasably engagable by a releasable feature such as a grabber or at least one frangible member on a delivery member in some mechanical constructions or, in other constructions, by at least one electrolytically severable element. Preferably, the control ring defines an inner passage through which at least one embolic coil is insertable into the aneurysm. In another construction, the occlusion device is held in place within the aneurysm by at least one vaso-occlusive structure such as a cage-like device.

Figure 1:
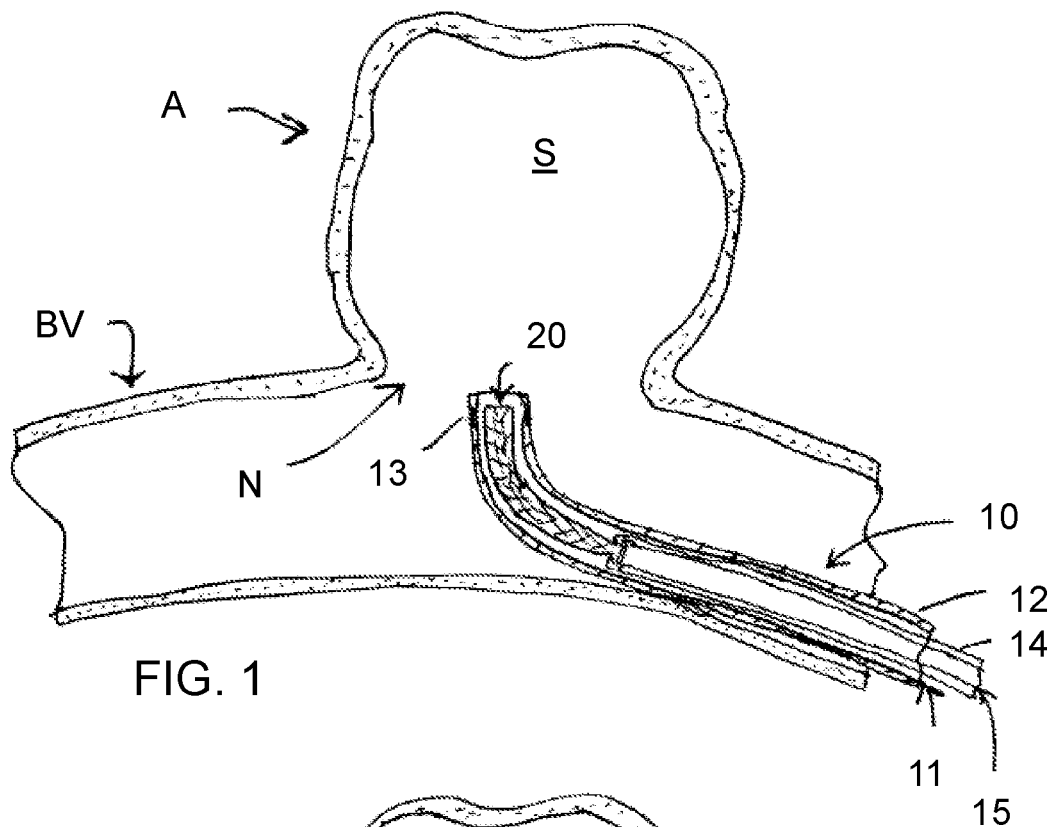
FIG. 1 is a schematic side cross-sectional view of an inventive occlusion device within a novel catheter delivery system positioned at the neck of an aneurysm of a blood vessel.

FIG. 1 schematically illustrates the distal portion of a novel delivery system 10 including a microcatheter 12 and a delivery tube 14 holding a tubular occlusion device 20 according to the present invention to be implanted within sac S of aneurysm A emerging from blood vessel BV. In one construction, the microcatheter 12 has a distal radiopaque marker band 13 and is advanced to the vicinity of neck N of aneurysm A such that marker band 13 is at the level of the neck N as seen under fluoroscopy.

Figure 2:
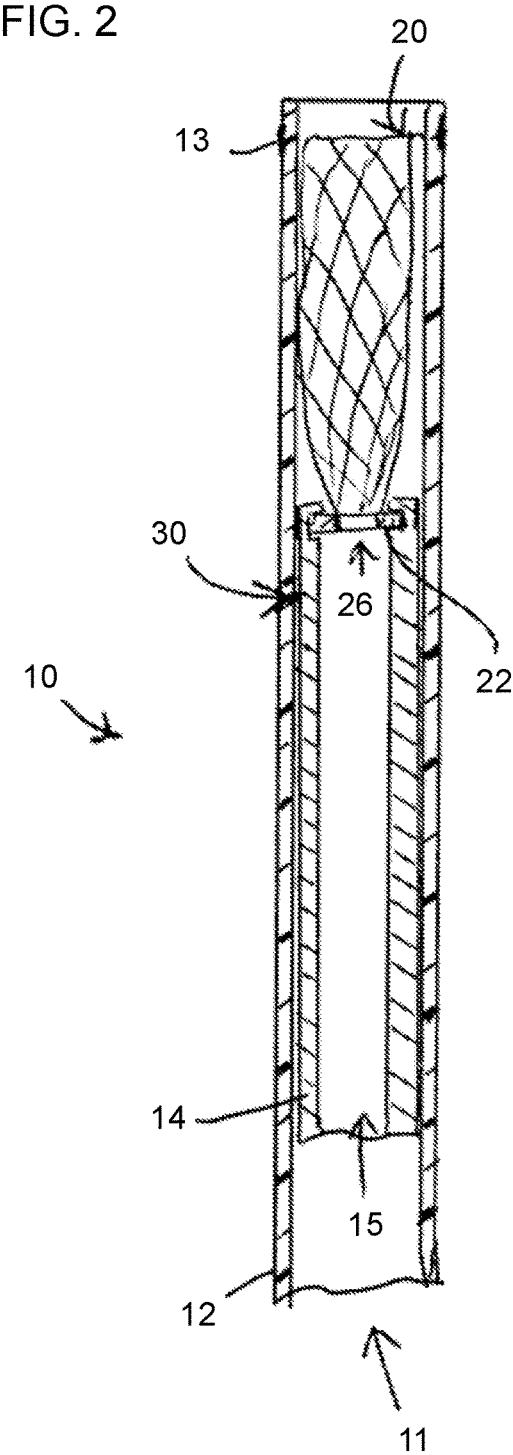
FIG. 2 is an enlarged schematic side view of the delivery system of FIG. 1 showing the occlusion device held in a collapsed condition.
Figure 5:
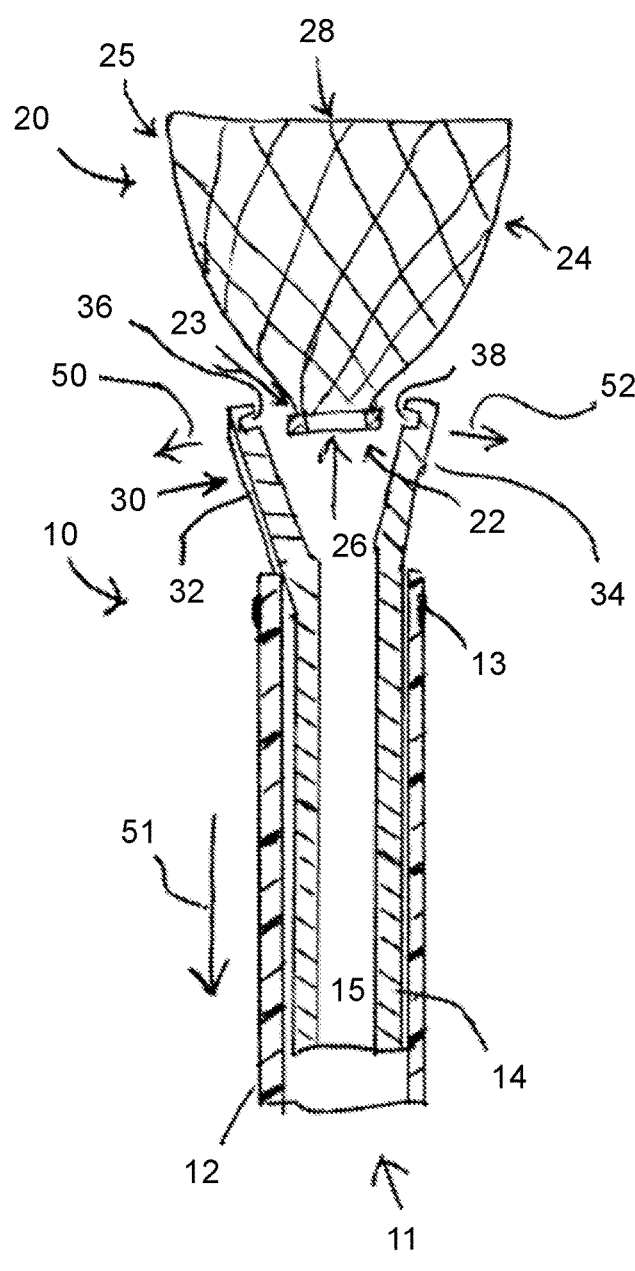
FIG. 5 is a schematic side view similar to FIG. 2 with the microcatheter withdrawn proximally to allow grasper fingers to release the control ring of the occlusion device.

Enlarged views of the distal portion of delivery system 10 and of occlusion device 20 are provided in FIGS. 2 and 5. Occlusion device 20 is shown in a second, collapsed condition in FIG. 2 within catheter lumen 11, with a control ring 22 held by grabber 30 of delivery tube 14. Control ring 22 is disposed about a proximal region 23 of device structure 25 and defines an inner passage 26 through which one or more embolic coils are inserted, as described in more detail below. Structure 25 of occlusion device 20 further includes a mesh body 24 and a distal region 28.

Figure 3:
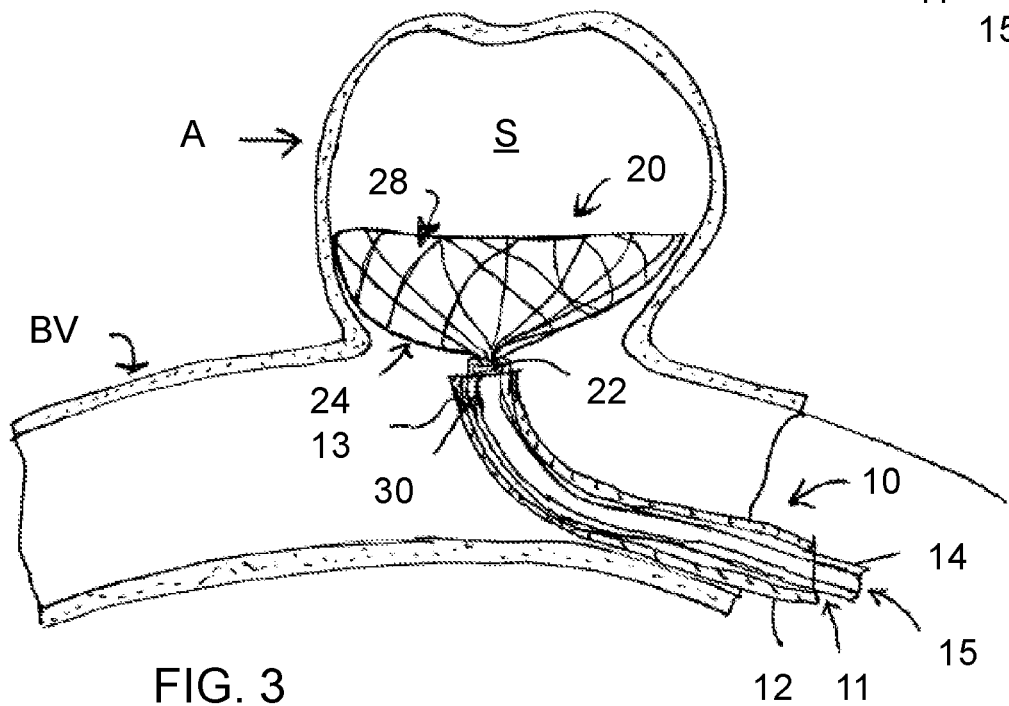
FIG. 3 is a schematic side view similar to FIG. 1 showing the occlusion device according to the present invention expanding within the sac of the aneurysm while still being securely held by the delivery system.

After the delivery system 10 is positioned as shown in FIG. 1, the delivery tube 14 is advanced within lumen 11 of catheter 12 to enable occlusion device 20 to expand into an approximately hemi-spherical shape within sac S as shown in FIG. 3. The shape of occlusion device 20 will conform to the shape of the sac S where device 20 touches the inner wall of the sac S. Grabber 30 continues to be constrained radially by lumen 11 of catheter 12 and maintains its grip on control ring 22 with a plurality of gripping regions such as notches 36 and 38, FIG. 5. In one construction, control ring 22 is radiopaque and is aligned under fluoroscopy relative to marker 13 on catheter 12 as shown in FIGS. 3 and 4.

Figure 4:
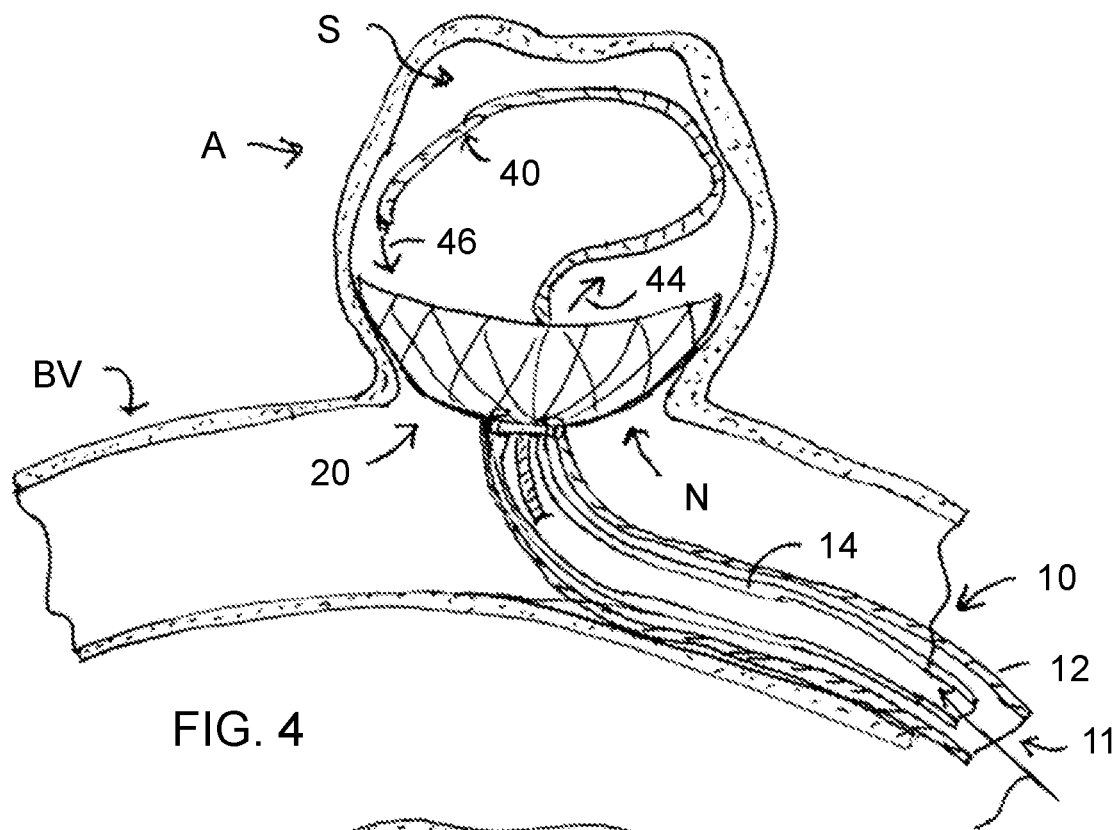
FIG. 4 is a schematic side view similar to FIG. 3 showing an embolic coil being advanced through the delivery system and the occlusion device into the aneurysm.
Figure 6:
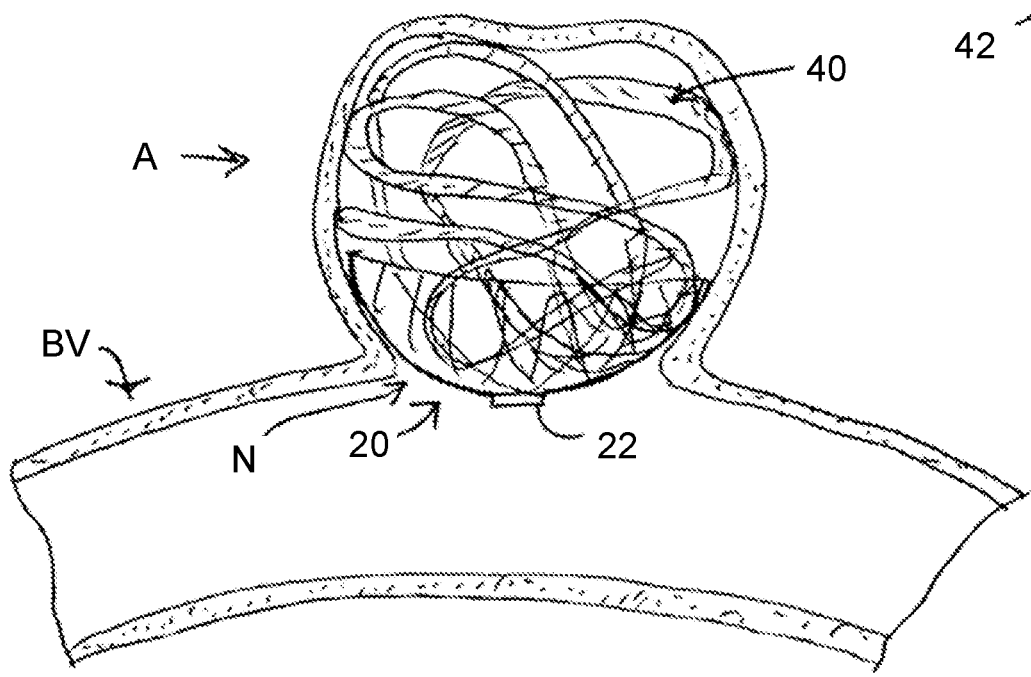
FIG. 6 is a schematic side cross-sectional view similar to FIG. 4 after the delivery system has been withdrawn and with embolic coils securing the occlusion device within the sac of the aneurysm.

Once occlusion device 20 is positioned within sac S, at least one embolic coil 40, FIG. 4, is advanced through lumen 15 of delivery tube 14 as indicated by arrow 42, through passage 26 of control ring 22 as indicated by arrow 44, and is advanced, arrow 46, within aneurysm A to substantially fill sac S and to anchor body 24 of occlusion device 20 against the interior wall of aneurysm A to block neck N as shown in FIG. 6.

After a sufficient amount of embolic coil 40 has been fully deployed within sac S to anchor occlusion device 20 within aneurysm A, the catheter 12 is withdrawn proximally, as indicated by arrow 51 in FIG. 5, while maintaining delivery tube 14 in place, to remove radial constraint on fingers 32 and 34 of grabber 30. Fingers 32 and 34 preferably are biased radially outwardly and move in the direction of arrows 50 and 52, respectively, to disengage control ring 22 from notches 36 and 38 in fingers 32 and 34, respectively.

In one construction, the catheter 12 is a polymeric microcatheter defining an inner lumen 11 having an inner diameter of between 0.020 inch and 0.027 inch, the delivery tube 14 has outer diameter that is slightly less than the inner diameter of the catheter lumen 11, and the grabber 30 with occlusion device 20 in the collapsed condition shown in FIGS. 1 and 2 also have outer diameters that are substantially the same as the inner diameter of the catheter lumen 11, which radially constrains fingers 32 and 34 to engage control ring 22. The lumen 15 of delivery tube 14 has a diameter capable of allowing passage of a conventional embolic coil delivery system having a nominal outer diameter of between 0.010 inch and 0.015 inch.

In some constructions, the delivery tube has at least one region of increased flexibility, especially near the distal end of the delivery tube, to minimize unintended microcatheter movement during translation of the delivery tube relative to the microcatheter. The at least one flexible region is made in one construction by laser-cutting a pattern of interrupted cuts into a medical-grade nitinol (NiTi) tube. In other constructions, a coiled metallic or polymeric cylindrical component and/or a cylindrical section of flexible polymeric material is added to the distal region of the delivery tube. The grabber is created in some constructions by laser-cutting material forming the grabber to create at least two finger elements, each preferably having a notch to enhance gripping of a control ring according to the present invention. In certain constructions, the grabber is integral, that is, is monolithically formed with the same material as the remainder of the delivery tube and, in other constructions, is fixedly attached to the distal end of the delivery tube.

In one construction, the structure 25 of occlusion device 20 is formed of metallic filaments that establish an expandable braided mesh tube. Suitable materials for the filaments include nitinol wires and other biocompatible metals, such as platinum, that will not remain in a collapsed condition after being ejected from a delivery tube. Preferably, at least one platinum wire is included for radiopacity. In other constructions, the structure 25 is formed of at least one polymeric material that does not become "set" in the collapsed condition.

Suitable materials for control ring 22 discussed above, and for control ring 22a and band 22b discussed below in relation to FIGS. 7-8B, include biocompatible radiopaque materials such as platinum, tantalum and gold. Other suitable metallic materials include cobalt chromium, stainless steel, and combinations of two or more of biocompatible metals. Suitable polymeric materials include biocompatible biodegradable and non-biodegradable materials, as described in more detail below.

One technique for manufacturing an occlusion device according to the present invention is illustrated in FIG. 7. After structure 25a is formed as a braided mesh tube, a control ring 22a is disposed by crimping and/or welding ring material about proximal region 23a to limit radial expansion at that site while defining an inner passage 26a through which one or more embolic coils can be inserted, as described above. Optionally, an inner sleeve such as a grommet (not shown) is inserted within structure 25a and positioned under the control ring 23a to maintain an inner diameter opening of desired dimension for inner passage 26a.

In this technique, a spherical mandrel 60 such as a steel ball bearing is inserted through distal region 28a to enlarge and expand the structure 25a in body region 24a. A clamp-like element such as a band 22b is then crimped over distal region 62 to further shape the body 24a. In some techniques, the assembly is heated to set mesh body 24a in the expanded condition.

When two hemispherical occlusion devices are desired, a cut is made along the circumference of mandrel 60, typically equidistant between control ring 22a and band 22b as indicated by dashed line 63, as well as on the opposite sides of control ring 22a and band 22b as shown by arrows 64 and 66, respectively. This technique creates two separate devices 20a and 20b, as depicted in FIGS. 8A and 8B, respectively. Distal end regions 28a and 28b are both open, such as illustrated for device 20 in FIGS. 1-6. Device 20b also has body 24b, proximal region 23b, and a passage 26b formed by band 22b which serves as a control ring according to the present invention. In other words, band 22b is incorporated into an implantable device 20b in one construction, instead of being a temporary clamp.

In alternative techniques, band 22b is removed and mandrel 60, FIG. 7, is extracted to form the occlusion device 20c, FIG. 9, with a constricted yet un-constrained distal region 28c, having a single control ring 22a. In yet another technique, a cut is made non-equatorially about structure 25a, such as along line 70, to generate device 20d, FIG. 10. In yet other constructions, a non-spherical mandrel such as a lozenge-shaped mandrel, is utilized to form an elongated device 20e, FIG. 11. In other words, the occlusion device according to the present invention can have many shapes such as round, elliptic, oblong, or otherwise asymmetric, and can have an open or a closed distal end. It is expected that an open distal end will typically allow better conformance to the neck and sac of the aneurysm to be treated.

Figure 12:
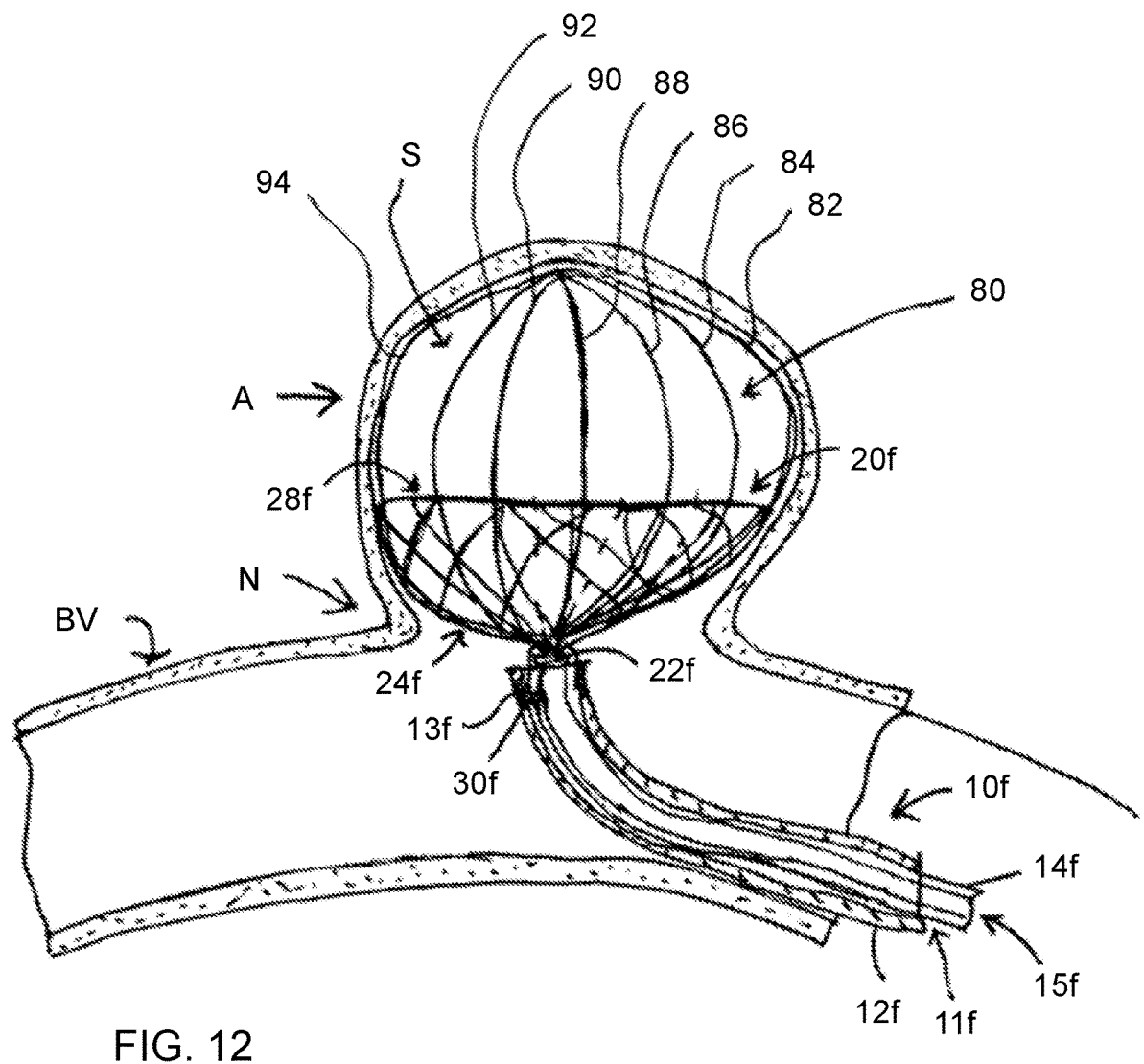
FIG. 12 is a view similar to FIG. 3 showing the occlusion device cooperating with a cage-like vaso-occlusive structure within an aneurysm.

An alternative occlusion device 20f according the present invention is illustrated in FIG. 12 cooperating with a cage-like vaso-occlusive structure 80 formed of strands 82, 84, 86, 88, 90, 92 and 94 in this construction. In some constructions, vaso-occlusive structure 80 is similar to one of the embodiments disclosed in U.S. Pat. No. 5,645,558 by Horton and, in certain other constructions, is similar to one of the embodiments disclosed in U.S. Pat. No. 5,916,235 by Guglielmi and in US Patent Publication No. 2010/0069948 by Veznedaroglu et al.

After a delivery system 10f is positioned as desired relative to aneurysm A, an elongated delivery member 14f is advanced within lumen 11f of catheter 12f to enable occlusion device 20f and vaso-occlusive structure 80 to expand within sac S as shown in FIG. 12. In this construction, a grabber 30f continues to be constrained radially by lumen 11f of catheter 12f and maintains its grip on control ring 22f with a plurality of gripping regions. In one construction, control ring 22f is radiopaque and is aligned under fluoroscopy in a similar manner as described above relative to FIGS. 3 and 4.

Once vaso-occlusive structure 80 is fully deployed in an expanded condition within sac S, structure 80 presses occlusion device 20f against the interior wall and across the neck N of aneurysm A to secure it in place. In other words, vaso-occlusive structure 80 serves in an expanded condition as a frame or lattice to anchor occlusion device 20f against neck N, and occlusion device 20f, held in place by structure 80, serves as a cover extending at least across neck N, the cover preferably being porous or otherwise defining sufficiently small openings, to enhance occlusion of aneurysm A. Preferably, occlusion device 20f is secured to vaso-occlusive structure 80 by at least one attachment point, being attached to at least one of a portion of the interior surface of device 20f and a portion of the control ring 22f, to maintain an aligned relationship between the device 20f and the structure 80, especially during loading and delivery of structure 80 and device 20f utilizing a delivery cannula.

In certain techniques, if a surgeon or other user desires to substantially fill the interior of sac S, at least one embolic coil is advanced through lumen 15f of delivery tube 14f, through a passage in control ring 22f, and then is advanced into aneurysm A. In other constructions, for use where insertion of one or more embolic coils is not desired, control ring 22f may lack a passage.

Figure 13:
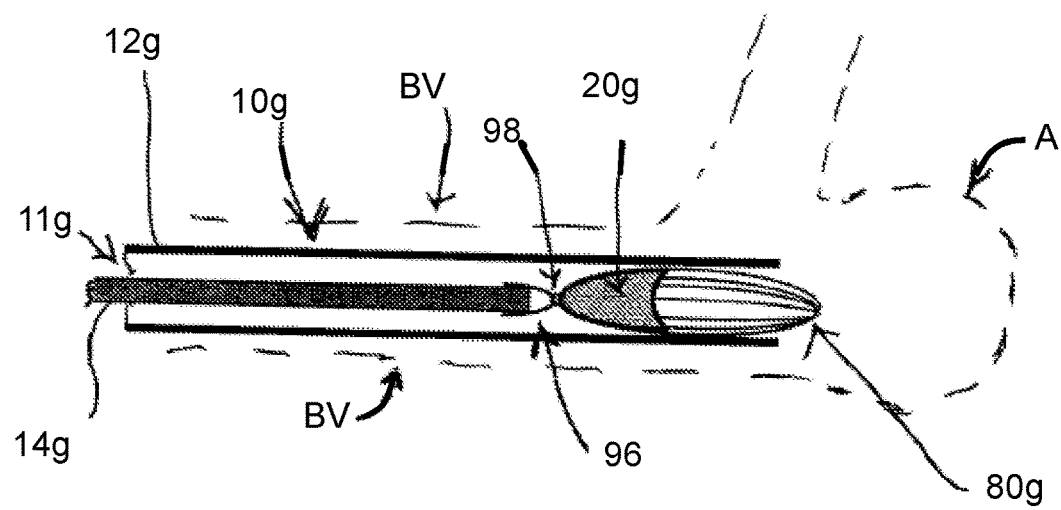
FIG. 13 is an enlarged schematic side view of an alternative delivery system for devices similar to those shown in FIG. 12 with an occlusion device and a vaso-occlusive structure held in a collapsed condition being advanced into an aneurysm.
Figure 14:
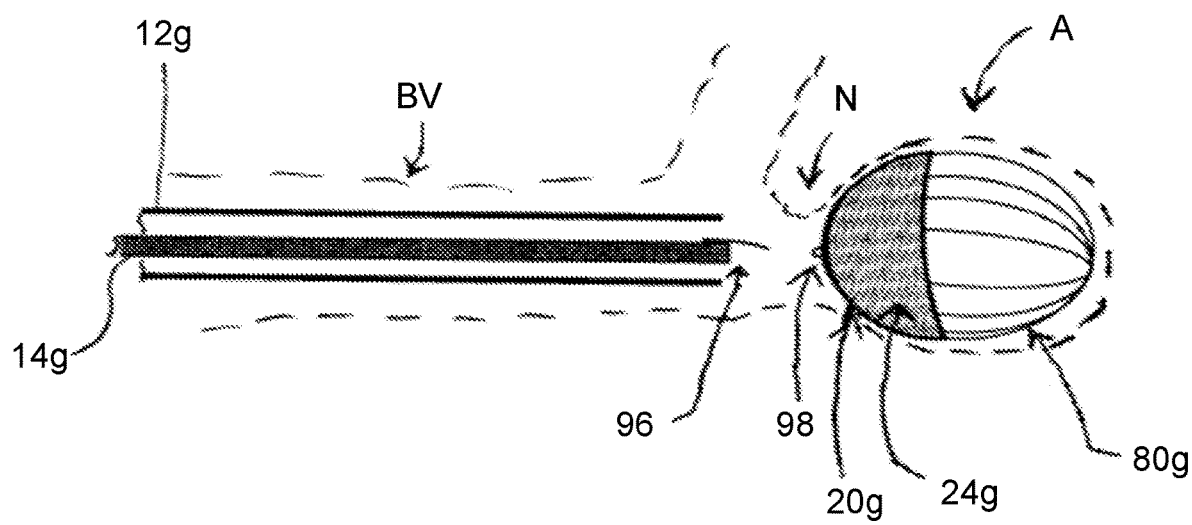
FIG. 14 is a schematic side cross-sectional view similar to FIG. 13 after the delivery system has been withdrawn, and with the vaso-occlusive structure securing the occlusion device within the sac of the aneurysm.

In yet other constructions, such as illustrated in FIGS. 13-14, an occlusion device 20g has a detachment feature 98, representing a conventional detachment joint, instead of a control ring. Examples of electrolytically severable joints and mechanical joints are described in U.S. Pat. No. 6,454,780 by Wallace and in U.S. Pat. No. 7,410,482 by Murphy et al., for example. Similar detachable joints are described in U.S. Pat. No. 5,916,235 by Guglielmi for cage-like vaso-occlusive structures.

After the delivery system 10g is positioned within blood vessel BV as shown in FIG. 13, a delivery member 14g, also referred to as a pusher 14g, is advanced within lumen 11g of catheter 12g to enable occlusion device 20g and vaso-occlusive structure 80g to expand within aneurysm A as shown in FIG. 14. The connection between severable element 96 and detachment feature 98 is then severed, mechanically and/or electrolytically.

Body 24g is formed of a wire mesh or braid in some constructions. In yet other constructions, the body of the occlusive device is a biocompatible film made from one or more polymeric substances. Suitable biocompatible compositions for film material include films or matrices of cellulose, alginate, cross-linked gels, and very thin polymer films of materials such as urethane, polycaprolactone (PCL), poly-lactic acid (PLA) and/or poly-glycolic acid (PGA). The film need not be erodible or bioabsorbable. In some constructions, microscopic pores or other openings are formed in the film having average diameters which are uniform in some constructions and non-uniform in other constructions. The geometric size of the pores is substantially constant along the length of the structure in some embodiments and, in other embodiments, varies along the length. The number of pores is substantially uniform along the length of the structure in some embodiments and, in other embodiments, varies along the length. Other potential materials include polysaccharides, colloidal compounds, and some lipid products. In an alternate configuration, at least the body of the occlusive device is made of a durable, non-erodible, non-bioabsorbable material, such as a solidified urethane foam or expanded polytetrafluoroethylene (PTFE). In some embodiments, the material defines openings at least 10 microns in diameter prior to implantation in the patient and has a thickness ranging between 10 microns to 500 microns.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An occlusion device system suitable for endovascular treatment of an aneurysm in a blood vessel in a patient, comprising:
   an occlusion device comprising:
      a substantially tubular structure comprising:
         a proximal end region,
         a distal end region,
         a first, expanded condition, and
         a second, collapsed condition comprising dimensions suitable for insertion through vasculature of the patient and through a neck of the aneurysm,
         the tubular structure comprising an exterior surface capable of contacting the aneurysm in the expanded condition and having an interior surface,
         the tubular structure being a braided mesh tube, the tubular structure having a hemispherical shape in the expanded condition, and
         the tubular structure being self-expanding to the expanded condition;
      a control ring having a substantially annular body disposed on the proximal end region of the tubular structure and at least substantially circumscribing the proximal end region to prevent radial expansion of the proximal end region and to provide an engagement feature during manipulation of the occlusion device;
   a delivery member comprising:
      an inner lumen; and
      a distal end region carrying a tubular grabber comprising at least two finger elements, each finger element comprising a notch having an inner top surface and an inner bottom surface defining an inner cavity having a height approximately equal to a thickness of the control ring such that the notch receives at least a portion of the control ring and thereby engages the control ring to the grabber; and
   a catheter comprising:
      a uniform inner diameter; and
      a catheter lumen sized from the inner diameter and configured to:
         completely enclose the substantially tubular structure, the control ring, and the grabber when the tubular structure is in the collapsed condition;
         constrict the grabber around the control ring so that the control ring is engaged within the notch of each finger element when at least a portion of the grabber is positioned within the catheter lumen; and allow the grabber to expand to disengage the control ring from the grabber once at least a portion of the grabber is outside the catheter lumen.

2. The occlusion device system of claim 1 wherein the control ring and the tubular grabber define an inner passage through which at least one embolic coil is insertable into the aneurysm.

3. The occlusion device system of claim 2 wherein the control ring includes an inner sleeve to define the inner passage.

4. The occlusion device system of claim 1 wherein the control ring is crimped onto the proximal end region.

5. The occlusion device system of claim 1 wherein the control ring includes radiopaque material.

6. The occlusion device system of claim 1 wherein the tubular structure includes a plurality of filaments.

7. The occlusion device system of claim 1 wherein the tubular structure defines a substantially enclosed volume.

8. The occlusion device system of claim 1 wherein at least a portion of the proximal end region of the tubular structure defines a plurality of openings having a sufficiently small size to enhance occlusion of the aneurysm.

9. The occlusion device of claim 1 further including a collapsible cage-like vaso-occlusive structure attached to at least one of a portion of the interior surface of the tubular structure and a portion of the control ring.

10. The occlusion device system of claim 1 wherein the delivery member is a tube formed of at least one metallic material.

11. The occlusion device system of claim 1 wherein the grabber is formed of a metallic material.

12. The occlusion device system of claim 1, wherein the tubular grabber is integral with the delivery tube.

13. A method of treating an aneurysm in a blood vessel in a patient, comprising:
  selecting an occlusion device comprising a substantially tubular structure having a proximal end region and a distal end region, having a first, expanded condition and a second, collapsed condition when drawn into a delivery catheter, and further including a control ring having a substantially annular body disposed on the proximal end region of the tubular structure and at least substantially circumscribing the proximal end region to prevent radial expansion of the proximal end region, the tubular structure being a braided mesh tube, the tubular structure having a hemispherical shape in the expanded condition;
  inserting the control ring into a notch of a finger element of a tubular grabber disposed at a distal end region of a delivery tube thereby engaging the control ring to the grabber, the notch having an inner top surface and an inner bottom surface defining an inner cavity having a height approximately equal to a thickness of the control ring;
  drawing the occlusion device engaged with the delivery tube into the delivery catheter to force the occlusion device into the collapsed condition;
  constraining the entire grabber in the delivery catheter;
  inserting the delivery catheter with the occlusion device into vasculature of the patient to reach the region of the aneurysm in the blood vessel;
  positioning the occlusion device within the aneurysm;
  partially withdrawing the delivery catheter to allow the braided mesh tube to self-expand to the expanded condition; and
  releasing the control ring from the notch and completely withdrawing the delivery catheter and the delivery tube from the patient comprising the step of extending the delivery tube so as the grabber is distal of the delivery catheter.

14. The method of claim 13 wherein the tubular structure includes braided filaments.

15. The method of claim 13 further including delivering at least one embolic coil through the delivery catheter and through the control ring to secure the occlusion device within the aneurysm to occlude flow into the aneurysm.

16. The method of claim 13 further comprising:
  mechanically engaging the control ring with the grabber to enable manipulation of the occlusion device, and
  utilizing the grabber to draw the occlusion device into the delivery catheter carrying the delivery tube to force the occlusion device into the collapsed condition.

17. The method of claim 13 further including selecting the occlusive device to be attached to a collapsible cage-like vaso-occlusive structure, and positioning the occlusive device within the aneurysm includes utilizing the vaso-occlusive structure to secure the proximal end region of the tubular structure across the neck of the aneurysm.

18. A method of treating an aneurysm in a blood vessel in a patient, comprising:
  selecting an occlusion device including a substantially tubular structure having a proximal end region and a distal end region, having a first, expanded condition and a second, collapsed condition when drawn into a microcatheter with a uniform diameter, at least a portion of the proximal end region defining a plurality of openings having a sufficiently small size to enhance occlusion of the aneurysm, and further including a control ring having a substantially annular body disposed on the proximal end region of the tubular structure and at least substantially circumscribing the proximal end region to prevent radial expansion of the proximal end region, the tubular structure is a braided mesh tube, the tubular structure having a hemispherical shape in the expanded condition;
  inserting the control ring into one or more notches of a tubular grabber on a delivery tube to enable manipulation of the occlusion device, the one or more notches having an inner top surface and an inner bottom surface defining an inner cavity having a height approximately equal to a thickness of the control ring, and drawing the entirety of the grabber into the microcatheter;
  drawing the occlusion device engaged with the delivery tube into the microcatheter carrying the delivery tube to force the occlusion device into the collapsed condition;
  inserting the microcatheter with the occlusion device into vasculature of the patient to reach the region of the aneurysm in the blood vessel;
  positioning the occlusion device within the aneurysm;
  partially withdrawing the microcatheter to allow the braided mesh tube to self-expand to the expanded condition;
  delivering at least one embolic coil through the delivery tube and through the control ring to secure the occlusion device within the aneurysm to occlude flow into the aneurysm;
  mechanically releasing the control ring by extending the grabber outside the microcatheter, thereby causing the grabber to expand to cause the control ring to exit the one or more notches; and
  completely withdrawing the microcatheter and the delivery tube from the patient.

* * * * *